(12) United States Patent
Vogtmeier et al.

(10) Patent No.: US 7,545,912 B2
(45) Date of Patent: Jun. 9, 2009

(54) X-RAY UNIT

(75) Inventors: Gereon Vogtmeier, Aachen (DE); Francisco Morales Serrano, Eindhoven (NL)

(73) Assignee: Koninklijke Philips Electronics N.V., Eindhoven (NL)

(*) Notice: Subject to any disclaimer, the term of this patent is extended or adjusted under 35 U.S.C. 154(b) by 0 days.

(21) Appl. No.: 10/573,743

(22) PCT Filed: Sep. 24, 2004

(86) PCT No.: PCT/IB2004/051847

§ 371 (c)(1),
(2), (4) Date: Oct. 16, 2006

(87) PCT Pub. No.: WO2005/032373

PCT Pub. Date: Apr. 14, 2005

(65) Prior Publication Data

US 2007/0206725 A1    Sep. 6, 2007

(30) Foreign Application Priority Data

Oct. 2, 2003    (EP)    ................................. 03103667

(51) Int. Cl.
*H05G 1/30* (2006.01)
*H05G 1/60* (2006.01)
*G01D 18/00* (2006.01)

(52) U.S. Cl. ............................... 378/95; 378/8; 378/207

(58) Field of Classification Search ............... 378/95, 378/205–208, 15, 20, 98, 162, 165, 166, 378/195
See application file for complete search history.

(56) References Cited

U.S. PATENT DOCUMENTS

| 4,896,343 | A  | * | 1/1990 | Saunders | 378/95 |
| 6,094,468 | A  |   | 7/2000 | Wilting et al. | |
| 6,666,579 | B2 | * | 12/2003 | Jensen | 378/197 |
| 6,708,054 | B2 | * | 3/2004 | Shukla et al. | 600/411 |
| 6,731,718 | B2 | * | 5/2004 | Ogura et al. | 378/63 |
| 7,054,412 | B2 | * | 5/2006 | Scheuering | 378/108 |
| 2001/0014140 | A1 | * | 8/2001 | Proksa et al. | 378/901 |

FOREIGN PATENT DOCUMENTS

DE    198024991 A1 *  7/1999
GB    1546926 A   *  5/1979

* cited by examiner

*Primary Examiner*—Irakli Kiknadze

(57) ABSTRACT

An X-ray unit according to the invention has a first arrangement (2) that is intended for the contactless and X-ray free measurement of first data of an object (1). A control unit (3) controls, on the basis of the first data of the object, a second arrangement (4) that measures X-ray data of the object by means of X-rays. With such an X-ray unit, first data 5 of the object can be obtained without using X-rays and control of the measurement of the X-ray data is made possible, with the result that, for the optimum quality of the X-ray data, only a minimum X-ray dose is applied to the object.

13 Claims, 3 Drawing Sheets

X-RAY UNIT

The invention relates to an X-ray unit and it relates to a method of measuring X-ray data of an object.

U.S. Pat. No. 6,094,468 discloses an X-ray unit that uses a so-called scanogram performed using X-rays in order to determine the thickness of the object. By means of said object thickness data, which are determined by the first radioscopy (scanogram), a second radioscopy using a higher X-ray dose is performed and, for instance, the X-ray intensity is controlled in this process as a function of the object thickness data in such a way that the X-ray data have an optimized signal-to-noise ratio with simultaneously minimized X-ray dose that is applied to the object.

It is an object of the present invention to provide an improved X-ray unit and an improved method of measuring X-ray data of an object.

The object is achieved by an X-ray unit comprising at least a first arrangement for the contactless and X-ray-free measurement of first data of an object, a second arrangement for measuring X-ray data of the object using X-rays and a control unit that is intended to control the second arrangement as a function of the first data.

An advantage of the X-ray unit according to the invention is that the measurement of the first data of the object is contactless and X-ray free and, therefore, no ionizing rays, such as X-rays or particles (for instance, electrons or alpha particles [$He^{2+}$]) that harm the patient are used. The term "X-rays" is here intended to be a synonym for ionizing radiation, in particular X-rays in the energy range of, for example, 5-1000 kiloelectronvolts (keV), gamma rays in the range 1-20 megaelectronvolts (MeV) and particle radiation (electrons, alpha-particles, protons, neutrons, charged atoms, etc.). Since the measurement is performed contactless, the patient is hardly affected and his position is also unaltered by contact with a measuring unit.

If, as described in U.S. Pat. No. 6,094,468, a scanogram is performed to determine first patient data using X-rays, this has the disadvantage that an X-ray dose that does not contribute to the X-ray picture has already to be applied to the patient at this point. In the case of an X-ray unit according to the invention, the necessary first data of the object is determined without using X-rays.

In the embodiment of an X-ray unit according to the invention as claimed in claim 2, light or sound is used to measure the first data. Light (for example, in the form of laser light) and sound (in particular, ultrasound) can easily be generated and do not contribute to the patient dose.

In accordance with the embodiment as claimed in claim 3, the first arrangement for measuring the first data of the object has a transmitter for transmitting light or sound and a receiver for receiving the reflected light or sound. In this case, in the case of light emitters, reference is made in particular to laser diodes and, in the case of sound, reference is made, in particular, to ultrasound transducers.

In the embodiment as claimed in claim 4, the first data are geometry data of the object. Geometry data are particularly easy to determine since only the outer contour of the object has to be measured It is unnecessary to penetrate the object (for instance, by means of light or sound) to determine an internal object model. An approximate determination of the object model can be achieved by scaling a standard object model to the particular object geometry, in which connection additionally known data about the object can also enter into the scaled object model.

In the embodiment as claimed in claim 5, the first arrangement is equipped to perform the determination of the first data of the object by means of triangulation, stereoscopy or transit-time determination.

In the embodiment of an X-ray unit according to the invention as claimed in claim 6, a measuring unit of the first arrangement is disposed in such a way that it can rotate around the object to be examined. This is advantageous since the measuring unit can measure the object from all sides during the rotation. A complete object measurement is thereby achieved.

In accordance with the embodiment as claimed in claim 7, the first arrangement comprises a plurality of spatially stationary measuring units. In this case, the first data of the object (for instance, geometry data) can be determined simultaneously by a plurality of measuring units. The stationary arrangement of the measuring units makes possible a simple calibration.

The embodiment specified in claim 8 is configured in such a way that an X-ray source of the second arrangement rotates around the object. X-ray data can then be recorded from various positions of the X-ray source. The X-ray intensity and/or the mean energy of the X-rays is controlled by the control unit.

In the embodiment as claimed in claim 9, there is a processor unit that is intended to convert the data measured by the first arrangement into geometry data. Such a conversion can, for example, comprise complicated scaling of predefined (three-dimensional) patient models.

The invention furthermore relates to a method as claimed in claim 10 for measuring X-ray data in which first data of an object are measured contactless and X-ray free and the first data serve to control the measurement of the X-ray data.

In claim 11 an embodiment of the method is described in which the measurement step of the first data is accomplished by means of light or sound and in which as an intermediate step in the measurement step the light or sound is reflected by a reflection-optimizing means that is provided on the object. This relates to an X-ray unit according to the invention in which the reflection properties of the object to be examined are improved by appropriate reflection-enhancing means.

These and other aspects of the invention are apparent from and will be elucidated with the embodiments described hereinafter.

Figure 1:
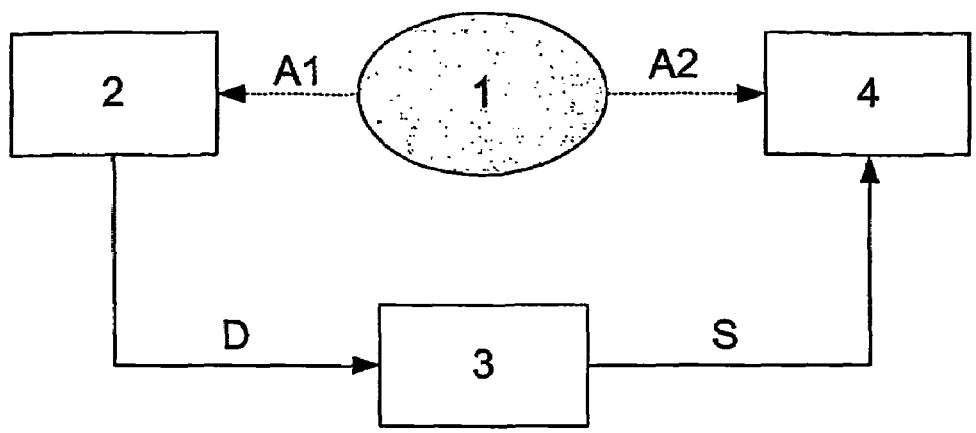
FIG. 1 shows a diagram of an X-ray unit according to the invention.

FIG. 1 shows diagrammatically the basic elements of an X-ray unit according to the invention. An object 1 (for example, a patient) is located in the examination region of the X-ray unit. A first arrangement 2 serves to measure contactlessly first data D of the object 1 in an X-ray-free manner. The data are obtained from the measured quantities A1. The measured quantities A1 are, for example, light-quanta distributions or sound-wave intensities that make it possible to determine object properties, that is to say, for example, light reflected by the object or reflected sound waves. Light quanta or sound waves are therefore carriers of information items about object properties. No X-rays are used to determine the first data of the object 1. This reduces the X-ray exposure for the patient. The control unit 3 is coupled to the first arrangement 2 and is fed the first data D. The control unit 3 is coupled to the second arrangement 4 and feeds it control signals S that controls the measurement of X-ray data performed using X-rays. The measured quantities A2 that are measured by the second arrangement are X-ray distributions. The control signals S serve to adjust parameters of the second arrangement adaptively.

X-ray measurements are often performed by means of X-rays from an X-ray source in which a metal anode is irradiated with electrons so that X-ray quanta are emitted to a maximum extent from the metal with the energy of the incident electrons. Such an X-ray source emits an X-ray spectrum whose intensity is determined by the X-ray-source current (that is to say, ultimately by the number of incident electrons) and that has a mean energy that depends on the X-ray source voltage, that is to say the energy of the incident electrons, on anode parameters, such as anode material and anode angle, and on the subsequent filtering of the X-rays.

Figure 2:
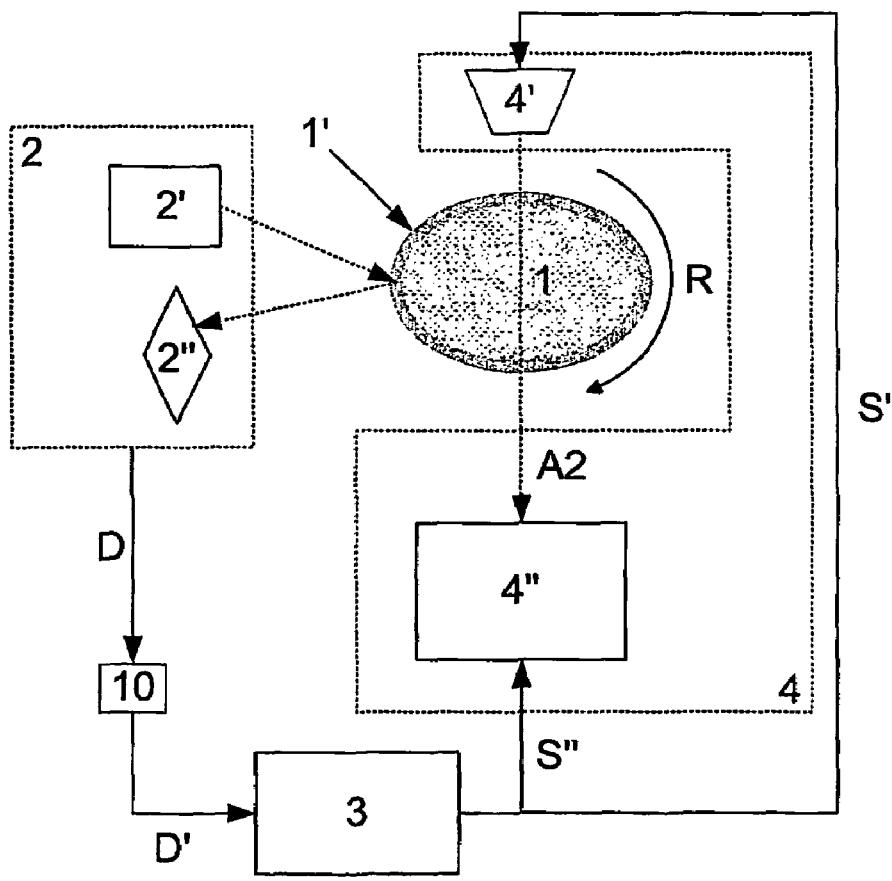
FIG. 2 shows an embodiment of an X-ray unit according to the invention.

In the embodiment shown in FIG. 2 of an X-ray unit according to the invention, the measured quantities A1 are light-quanta intensities (in particular, of reflected laser light) that are generated by the first arrangement 2 in a transmitter 2' (for example, a laser diode) are reflected by the object 1 and are then measured by a receiver 2" (for example, a detector with one-dimensional or two-dimensional spatial resolution for measuring light intensities). In this way, the distance from the reflecting surface can be determined by means of active triangulation. To enhance the reflection properties, the object (for example, a patient) may also be provided with reflection-optimizing means 1', for example by wrapping in a reflecting thin foil or by spraying-on a reflecting layer. The control unit 3 is coupled to the first arrangement 2 and is fed the first data D. In the embodiment shown, there is, between the first arrangement 2 and control unit 3, a processor unit 10 that converts the measured data D into object thickness data D' of the object 1. Object thickness data are geometry thickness data of the object. The processor unit 10 may either be an independent unit, as shown in FIG. 2, or it may be integrated in the first arrangement 2 or in the control unit 3, or it may comprise a plurality of processing components that are optionally distributed over the first arrangement 2 and the control unit 3.

The control unit 3 starts the measurement of the X-ray data by the second arrangement 4 by means of the control signals S' and S". The second arrangement has an X-ray source 4' and an X-ray detector 4" in the embodiment shown. If the X-ray unit is a computer tomograph, then, to measure the X-ray data of the object 1, the X-ray source 4' and the X-ray detector 4" are rotated in the direction R around the object 1 and, in each case, X-ray data (so-called X-ray profiles) are measured at different angles of rotation. The X-ray data measured in this process are X-ray transmission data and reproduce the X-ray absorption properties of the object 1. The X-ray transmission data are fed to a reconstruction unit, which is not shown, that calculates sectional pictures of the X-ray absorption properties of the irradiated object from said data. In the case of large object thicknesses or in the case of low power of the X-ray source 4', the intensity of the transmitted X-rays measured at the X-ray detector 4" may be so low that the measurement is impaired by high noise. In the case of unduly high power of the X-ray source 4' or in the case of low object thicknesses, the intensity of the measured X-rays may be higher than would have been necessary for a qualitatively adequate measurement. This then results in an unnecessary application of X-rays to the object 1 (the patient). Depending on the object thickness data D', from which the control unit 3 can calculate, for a given position of the X-ray source 4' how high the necessary intensity and/or mean energy of the X-rays have/has to be for qualitatively adequate measurement, the control unit 3 regulates by means of the control signals S' the X-ray intensity, for example, by varying the X-ray-source current or by varying the X-ray source voltage. Such control mechanisms are known to the person skilled in the art. In the case of a non-rotating X-ray unit that only makes X-ray projection pictures at one given angle, for instance by means of a two-dimensionally resolving X-ray detector, the control unit may also control a local variation in the X-ray intensity using the object thickness data, for instance by inserting X-ray filter elements into the beam path. It may also be expedient for the control unit 3 to control parameters of the X-ray detector 4" by means of control signals 3". Such parameters may be, for example, the duration of the individual measurements or the local binning, that is to say the locally dependent combination, of detector elements to form an effective detector element of larger area in order to obtain a better signal-to-noise ratio in this way.

Instead of comprising a laser diode 2' and a detector 2" for active triangulation measurement, the first arrangement 2 may also be configured differently. Examples of this are:
  a scanner comprising a transmitter and receiver for transit-time determination of the emitted signal (either by means of laser light or sound waves),
  a transmitter for radiating a known light pattern (for example, a geometrical grid) and a camera for evaluating the pattern deformation on the object surface,
  a binocular or trinocular camera system for passive triangulation measurement (stereoscopy with ambient light),
  a contactless acoustic distance sensor, in particular with a narrow sound lobe.

Optical and acoustic distance sensors are known to the person skilled in the art and are provided, for instance, by Baumer Electric AG, LAP GmbH or Micro-Epsilon Messtechnik. A review lecture on distance sensors by Prof R Dillmann of the University of Karlsruhe is to be found, for example, on the Internet page: http://wwwiaim.ira.uka.de/Teaching/VorlesungRobotikIII.

Figure 3:
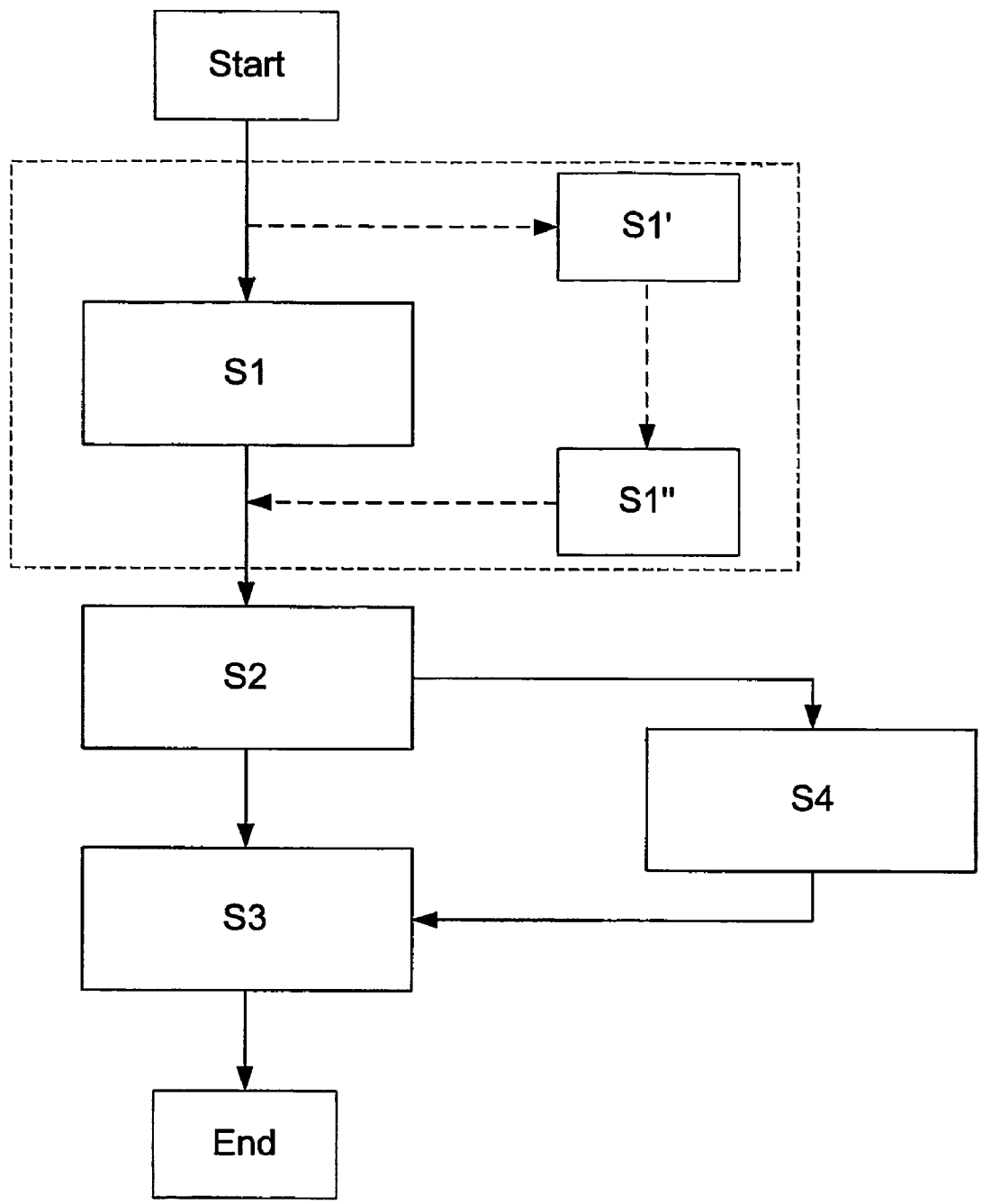
FIG. 3 shows a flow chart of a method according to the invention of measuring X-ray data and FIG. 4 shows a diagram of a computer tomograph according to the invention comprising stationary measuring units.

FIG. 3 shows diagrammatically a flow chart of a method of measuring X-ray data of an object. First, the method is started. Then, the first data of the object are measured in method step S1. In the case of an embodiment comprising a first arrangement for measuring the first data that has a transmitter and a receiver, method step S1 subdivides into the method steps S1' and S1", a carrier (for example, light or sound) being transmitted by the transmitter in S1' and the receiver measuring the reflected or re-radiated carrier in S1". In this procedure, the method step S1 or the method steps S1' and S1", are repeated as often as necessary (for example, if the object is scanned or if the object is measured from different positions), which is indicated by the broken frame. The reflection of the carrier (e.g. light or sound) by the object can thereby be enhanced through a reflection-optimizing means (e.g. as described above by wrapping the object in a thin reflection foil or by spraying-on a reflection layer on the object). In method step S2, an X-ray measurement protocol is determined from the measured first data. The X-ray measurement protocol defines, for example, the intensity and/or the mean energy of the X-rays at different positions of the X-ray source or the X-ray intensity distribution in the one-dimensionally or two-dimensionally propagated X-rays. In method step S3, the X-ray data of the object are measured, control signals being delivered to the second arrangement in method step S4 so that the X-ray measurement protocol is adhered to. The control signals serve, inter alia, to start the X-ray measurement, to adjust the X-ray intensity and mean energy of the X-ray spectrum and/or to undertake the desired filtering in the X-ray beam, for example, by inserting X-ray filter elements. Method steps S3 and S4 therefore typically proceed simultaneously. If the X-ray data of a larger object are measured, the method steps S1 or S1' and S1" may also proceed simultaneously with S2, S3 and S4, the first data of an object region then being measured from which X-ray data are measured only at a later instant in time.

Figure 4:
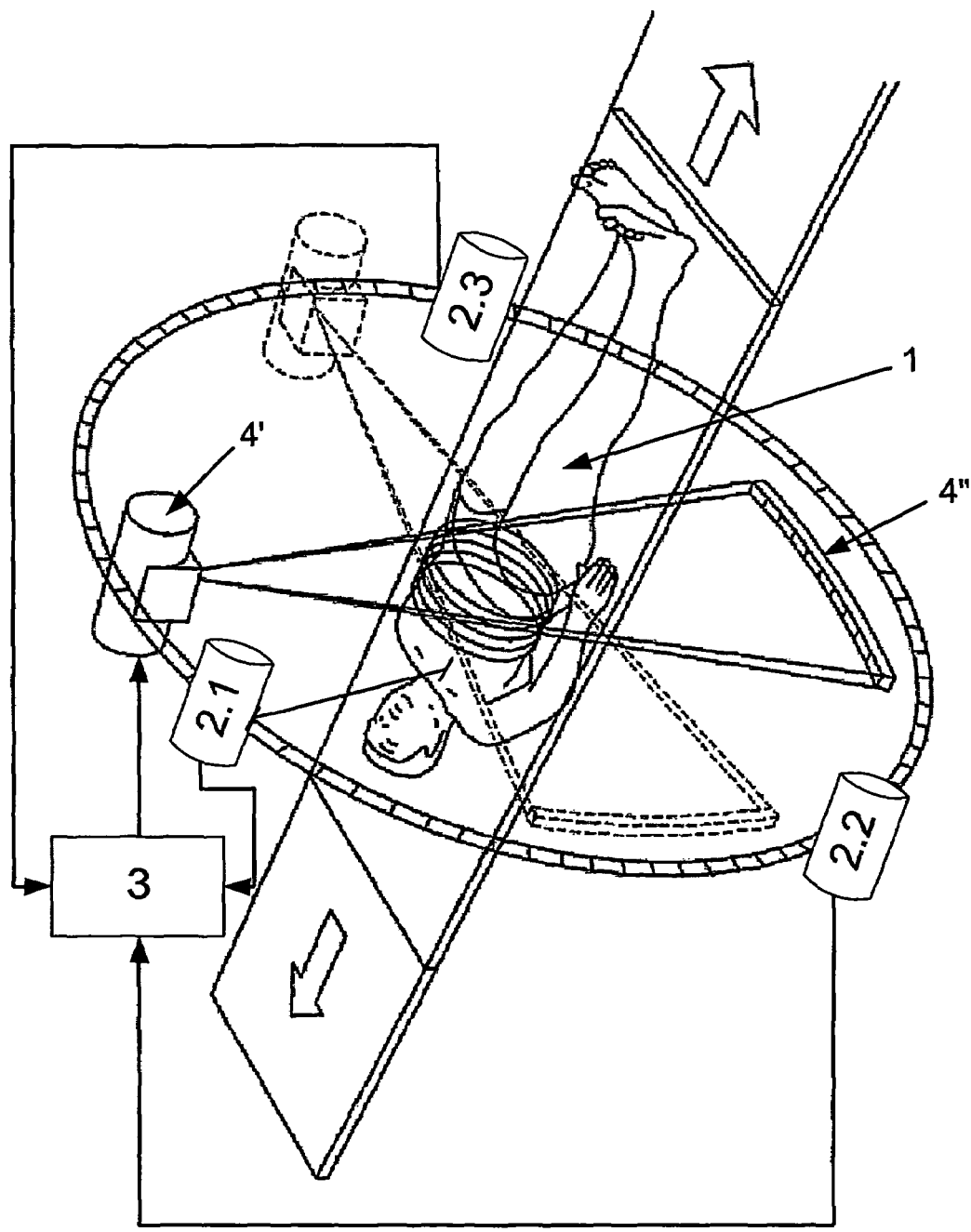

FIG. 4 shows diagrammatically a structure of an X-ray unit according to the invention that comprises a second arrangement 4 having an X-ray source 4' and an X-ray detector 4". The X-ray source 4' and the X-ray detector 4" are attached to a mechanical structure, which is not shown (rotor of the gantry of the computer tomograph) so that X-ray tube 4' and X-ray detector 4" rotate simultaneously around the patient 1. The X-ray unit furthermore has a first arrangement 2 comprising three non-rotating measuring units 2.1, 2.2, 2.3 that are mounted, for example, on the non-rotating part of the gantry (stator). The measuring units 2.1, 2.2, 2.3 measure the patient geometry by means of a linear or two-dimensional laser distance sensor. The three measuring units 2.1, 2.2, 2.3 are disposed in such a way that they can completely cover the patient 1. In the embodiment shown in FIG. 4, the patient 1 is positioned on a patient table. The geometry of said table may have already been measured beforehand without a patient or may be known to the X-ray unit (for example, in the form of an electronically stored table). It is then possible to subtract the table geometry from the measured total geometry and, in this way, to determine the patient geometry that is important for the dose calculation. This takes place in a suitable processor unit 10. Furthermore, the processor unit 10 may serve the purpose of using the measured object thickness data, for example to adapt exemplary patient models to the measured patient geometry. An exemplary patient model may comprise for example, lung, liver, bones, etc. of a patient. Optionally, the patient model may be adapted to the actual situation by selecting parameters, such as body-fat components, bone thickness, etc. before it is scaled to the measured patient geometry. This model for estimating the arrangement of strongly absorbing regions (bones) or weakly absorbing regions (lung) or regions requiring a high contrast resolution (liver) enables a fine tuning of the X-ray measurement protocol to be performed. For further details, reference is made to U.S. Pat. No. 6,094,468.

In a further embodiment, however, the X-ray unit may also be provided with only one measuring unit 2', which is mounted in a concomitantly rotating manner on the mechanical structure. To determine the geometry data (object thickness data), the measuring unit 2' is then rotated around the patient. The patient geometry is determined from distance data recorded at different angles.

In the case of an X-ray unit according to the invention as shown in FIG. 4, there are various methods of operating it. Thus, in one embodiment, the measuring units 2.1, 2.2, 2.3 are disposed in such a way that they determine the geometry of a patient region before said patient region is radioscoped by means of X-rays. Measurement of the patient geometry and X-ray radioscopy can then take place simultaneously for different patient regions. However, it is also possible to measure the patient first as a whole using the measuring units 2.1, 2.2, 2.3, the patient being passed through the measurement region of the measuring units on the patient table before the measurement of the X-ray data is performed.

The invention claimed is:

1. An X-ray unit comprising at least a first arrangement for contactless and X-ray-free measurement of first data of an object, the first data comprising at least one thickness measurement of the object, said at least one thickness measurement of the object derived from a measured distance to at least two positions on the surface of the object, a second arrangement for measuring X-ray data of the object using X-rays, and a control unit that is provided for controlling the second arrangement as a function of the first data, wherein at least one of intensity and mean energy of the X-rays is controlled by the control unit based at least in part on the first data.

2. An X-ray unit as claimed in claim 1, wherein the first arrangement comprises a plurality of distance measuring units spatially distributed that are stationary with respect to the object.

3. An X-ray unit as claimed in claim 1, wherein the first arrangement comprises a transmitter for transmitting light or sound and a receiver for receiving the reflected light or sound.

4. An X-ray unit as claimed in claim 1, wherein the first data are geometry data of the object.

5. An X-ray unit as claimed in claim 1, wherein the first arrangement is designed to measure the first data by triangulation.

6. An X-ray unit as claimed in claim 1, wherein the first arrangement has a measuring unit designed to rotate around the object.

7. An X-ray unit as claimed in claim 1, wherein the second arrangement has an X-ray source designed to rotate around the object.

8. An X-ray unit as claimed in claim 1, wherein the X-ray unit comprises a processor unit that is intended to convert data measured in the first arrangement into geometry data.

9. A method of measuring X-ray data of an object that comprises the following steps:
    measuring of first data of the object, the first data comprising at least one thickness measurement of the object, said at least one thickness measurement of the object derived from a measured distance from a first arrangement by means of a contactless and X-ray-free measurement of first data of the object to at least two positions on the surface of the object,
    obtaining X-ray data of the object by means of X-rays from an emitter that rotates with respect to the object, and
    controlling the measurement of the X-ray data as a function of the first data, wherein at least one of intensity and mean energy of the X-rays is controlled based at least in part on the first data.

10. A method according to claim 9 in which the step of measuring the first data of is accomplished by means of sound or light, whereby as an intermediate step in the measurement step the light or sound is reflected by a reflection-optimizing means that is provided on the object.

11. The method of claim 9, further comprising determining the first data by triangulation.

12. The method of claim 9, further comprising determining a geometry of the object from the first data.

13. The method of claim 9, further comprising determining the geometry of the object based on the first data and a geometry of a support structure for the object.

* * * * *